United States Patent [19]

Gangneux

[11] 4,089,836

[45] * May 16, 1978

[54] PROCESS FOR THE COLORATION OF POLYAMIDES WITH PIGMENTS DERIVED FROM CARBOXYAMIDO-POLYIMIDES

[75] Inventor: Philippe Yves Edouard Gangneux, Bihorel, France

[73] Assignee: Produits Chimiques Ugine Kuhlmann, Paris, France

[*] Notice: The portion of the term of this patent subsequent to Jan. 11, 1994, has been disclaimed.

[21] Appl. No.: 601,960

[22] Filed: Aug. 4, 1975

Related U.S. Application Data

[63] Continuation of Ser. No. 330,344, Feb. 7, 1973, abandoned, and a continuation of Ser. No. 330,332, Feb. 7, 1973, Pat. No. 4,002,591.

[30] Foreign Application Priority Data

Feb. 7, 1972  France ............................... 72.03975
Feb. 7, 1972  France ............................... 72.03976

[51] Int. Cl.² .............................................. C08K 5/34
[52] U.S. Cl. ............................ 260/37 N; 260/78 TF
[58] Field of Search ............. 260/37 N, 78 R, 78 TF, 260/281, 326 R, 326 C

[56] References Cited

U.S. PATENT DOCUMENTS 2,668,815   2/1954   Nawiasky ........................... 260/281
3,658,747   4/1972   Kolyer ............................... 260/37 N
3,809,670   5/1974   Costain ............................. 260/37 N

FOREIGN PATENT DOCUMENTS 986,556   3/1965   United Kingdom.

*Primary Examiner*—Paul R. Michl
*Attorney, Agent, or Firm*—Beveridge, DeGrandi, Kline & Lunsford

[57] ABSTRACT

Linear polyamides are colored with pigments of the formula:

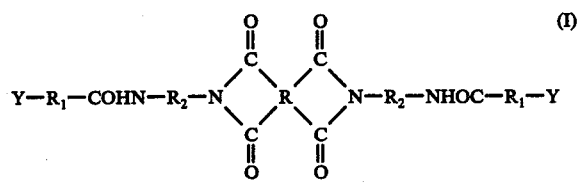

wherein R represents the tetravalent residue of a substituted mono- or poly-cyclic aromatic hydrocarbon or a substituted or unsubstituted perinone, $R_1$ represents a substituted or unsubstituted aliphatic, benzene, naphthalene or heterocyclic radical, $R_2$ represents a substituted or unsubstituted aliphatic, aromatic or heterocyclic radical and Y represents an amino or haloformyl group. A copolycondensate results.

10 Claims, No Drawings

PROCESS FOR THE COLORATION OF POLYAMIDES WITH PIGMENTS DERIVED FROM CARBOXYAMIDO-POLYIMIDES

This application is a continuation of application Ser. No. 330,344, filed Feb. 7, 1973, now abandoned, and a continuation of application Ser. No. 330,332, filed Feb. 7, 1973 now U.S. Pat. No. 4,002,591. The entire disclosure of each of these applications is relied upon and incorporated herein by reference.

This invention relates to a process for the coloration of linear polyamide fibers by means of pigments copolycondensed in the polymer chain, and to copolycondensates obtained thereby.

It is known to use dyestuffs containing reactive groups in order to color bulk fibers based on polyamides. These groups partially fix the dyestuff on the polymer formed or on the polymer in the course of formation.

When the dyestuffs have only one functional group capable of reacting with an amino or carboxy group of the polymer during its formation, the fixation of the dyestuff may stop the process of polycondensation on the end of the chain. When the dyestuffs have three or more groups capable of reacting, the polycondensation gives rise to a network system which may be polydimensional.

By means of the present invention, these modifications of the polycondensation process may be avoided, and linear polyamides produced in which the dyestuff material forms part of the polycondensed chain.

According to the present invention, a process for the coloration of a linear polymer is provided which comprises effecting the polycondensation of the monomer in the presence of a pigment of the polycyclic polycarboximide series containing two primary amine or haloformyl functional groups.

More particularly, the present invention provides a process for the coloration of a linear polyamide which comprises effecting the polycondensation of the amide monomer or monomers in the presence of a pigment of the polycyclic polycarboximide series contaiing 2 primary amine or haloformyl functional groups, wherein the pigment has the formula:

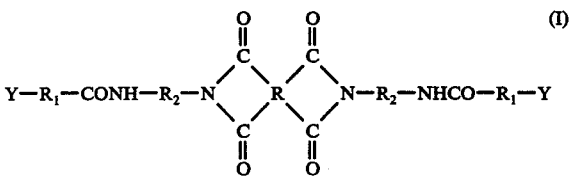

(I)

wherein R represents the tetravalent residue of a substituted mono- or poly-cyclic aromatic hydrocarbon or a substituted or unsubstituted perinone; $R_1$ represents a substituted or unsubstituted aliphatic, benzene, naphthalene or heterocyclic radical; $R_2$ represents a substituted or unsubstituted aliphatic, aromatic or heterocyclic radical; and Y represents an amino or haloformyl group.

This invention also provides a process for the coloration of a linear polyamide which comprises effecting the polycondensation of the amide monomer or monomers in the presence of a pigment obtained by condensing a compound of the formula (I), wherein Y is a haloformyl group, with a diamine of the formula:

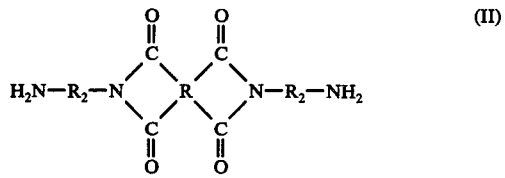

(II)

wherein R and $R_2$ have the meanings given above.

This invention also provides the copolycondensates resulting from the processes of this invention.

According to the invention, hydrocarbons comprising the benzenic, naphthalenic, anthracenic, phenanthrenic, naphtacenic or perylenic nucleus, are aromatic hydrocarbons. For instance, phenylbenzophenone is an aromatic hydrocarbon.

Aliphatic radicals more particularly involve linear hydrocarbons having from 1 to 10 carbon atoms. Alkyl groups or alkoxy groups preferably comprise from 1 to 5 carbon atoms.

As $R_1$ or $R_2$ are considered, possible heterocycles are, for instance, 2,6-benzobisthiazoldiyl, 2,7-benzobisthiazoldiyl, 2,6-[9,10-dichlorotriphenodioxazindiyl]. The radical R may have up to 4 substitutents, and preferably 2. $R_1$ may bear up to 4 substituents, and $R_2$ up to 2 substituents.

Examples of substituents of R are halogen atoms or nitro, hydroxy, or alkoxy groups and examples of substituents of $R_2$ are halogen atoms or nitro, alkyl or alkoxy groups.

The preferred monoamino-monocarboxylic acid used for the copolycondensation is 11-amino-undecanoic acid; E-caprolactam; the preferred diamines are p-phenylenediamine, decamethylene-diamine and hexamethylenediamine, and the preferred diacids are terephthalic, isophthalic, adipic and sebacic acids.

The linear polyamides may be obtained for example by several processes, such as polycondensation of a monoaminomonocarboxylic acid or of the corresponding lactam, polycondensation of a diamine and a diacid in equimolecular proportions, polycondensation of the salt resulting from the reaction of a diamine and a diacid. In the starting materials the two functional groups are separated by at least two carbon atoms.

Diamines of the general formula (II) and suitable pigments are described in my patent application entitled "Amino-imide Pigments" (Ref. A 714/P), Ser. No. 330,345, filed Feb. 7, 1973, now abandoned, and my patent application entitled "Pigmentary Imido-perinones" (Ref. A 709/P), Ser. No. 330,331, filed Feb. 7, 1973, now abandoned.

The compounds of formula (I) may be prepared, for example, by reacting an acid halide of the general formula:

$$Y - R_1 - CO\ Hal \qquad (III)$$

with a diamine of formula (II); preferably at least two moles of monohalide and five or six moles of dihalide are used per mole of diamine.

Examples of halides of formula (III) are the acid chloride of p-aminobenzoic acid, terephthaloyl dichloride, adipoyl dichloride and sebacoyl dichloride.

The reaction is effected at a temperature above 150° C, preferably between 200° C and 250° C, in a solvent medium. It is preferably carried out in the presence of an agent capable of fixing the halohydric acid, such as for example a tertiary base or an alkali metal carbonate.

The reaction of the dyestuff of formula (I) in which Y represents a haloformyl group with the diamine of formula (II) or other diamines enables a large number of various pigments covering a very extensive range of different shades to be obtained for a single chemical structure of the type (I).

The pigments are compounds insoluble in organic solvents, and stable at high temperature, for example, at a temperature higher than 300° C and possibly higher than 350° C, slightly soluble in concentrated sulfuric acid, but soluble in monomers in the molten state. After a possible grinding which gives them a very finely divided form, they are suitable for the coloration of synthetic fibers.

In order to carry out the process according to the invention, the monomers and dyestuffs are mixed and the copolycondensation is effected by the usual processes for the preparation of polymers. The proportions of the dyestuff may vary from 1% (i.e., 1 per 1000) to 2% of the weight of the monomer.

The introduction of dyestuff characteristics into the polymer chains modifies the viscosity and the molar mass of the polymers. These modifications are variable according to the pigments used and the optimal amounts of pigment may be determined experimentally.

The copolycondensates may be spun according to the usual techniques. Microscopic examination of the fibers shows that the coloration is perfectly homogeneous. On the other hand, it has proved impossible to separate the dyestuff and the polymer by extraction with solvents for the polymers, such as formic acid or metacresol in the case of polyamides. Finally, the viscosity measurements carried out on the solutions in formic acid of polymers obtained by introducing variable percentages of dyestuff monomers show that there is indeed polycondensation. The examination of the viscosity curves for the colored polymers in the molten state leads to the same conclusion.

In the following Examples, which are purely illustrative, the parts are parts by weight.

EXAMPLE 1

5 parts of N,N'-bis(4'-amino-biphenyl)-perylene-3,4,9,10-bis(dicarboximide) are heated with stirring with 3 parts of 4-amino-benzoic acid chloride in 150 parts of nitrobenzene at 210° C until reaction is complete. After cooling, the precipitate is filtered off. This is washed with nitro-benzene, taken up in acetone or methanol, again filtered, taken up in ethyl ether, filtered, and dried. The N,N'-bis(4-amino-benzoyl) derivative of the starting diamine is obtained with a theoretical yield, and is a brown red product with a melting point above 350° C.

EXAMPLE 2

5 parts of N,N'-bis(4-amino-2-or 3-nitrophenyl)-benzene-1,2,4,5-bis(dicarboximide) are heated with stirring with 4 parts of 4-amino-benzoic acid chloride in 100 parts of nitrobenzene at 210° C until reaction is complete. The N,N'-bis(4-amino-benzoyl) derivative of the starting diamine is obtained with a theoretical yield, and is a yellow product with a melting point above 350° C.

EXAMPLE 3

4 parts of N,N'-bis(4-amino-2-or 3-nitrophenyl)-1,5,4,8-bis(dicarboximido)-naphthalene are heated while stirring with 6 parts of terephthaloyl dichloride in 100 parts of nitrobenzene at 210° C until reaction is complete. A yellow product with a melting point above 350° C is obtained with a theoretical yield. This product is the N,N'-bis-(4-chlorocarbonyl-benzoyl) derivative of the starting diamine.

2 parts of the dichloride thus obtained, in a very finely divided form, 3 parts of N,N'-bis(4-amino-2-or 3-methylphenyl)-3,4-9,10-bis(dicarboximide)-perylene and 0.5 parts of potassium carbonate in 100 parts of nitrobenzene are heated while stirring at 210° C for 15 hours. The hexa-imide is obtained in a theoretical yield, and is an orange-red product with a melting point above 350° C.

EXAMPLE 4

2 parts of the mixture consisting of the cis form of the compound of formula:

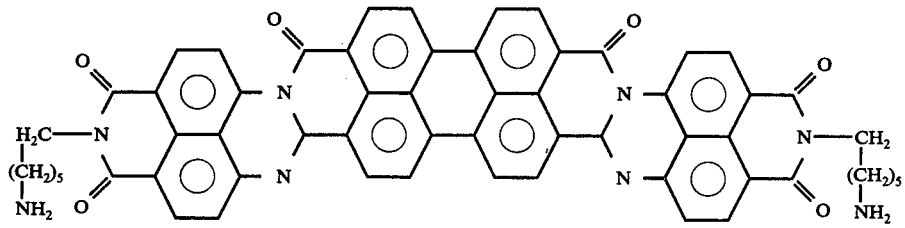

and the trans form of the same perinone are heated while stirring with 2 parts of adipoyl dichloride in 80 parts of nitrobenzene at 210° C until reaction is complete. A blue product with a melting point above 350° C is obtained with a theoretical yield. This compound is the N,N'-bis(5-chloroformyl-pentanoyl) derivative of the starting diamine.

EXAMPLE 5

49.95 parts of hexamethylene-ammonium adipate are intimately mixed with 0.05 parts of an equimolecular mixture of N,N'-bis(4-amino-phenyl)-3,4,9,10-bis(dicarboximide) perylene and adipic acid. The composition is introduced into an autoclave, which is closed and purged with nitrogen. The temperature is raised to 180° C over a period of one hour and maintained at this temperature for half an hour. After decompression, the autoclave is scavenged with nitrogen and heated to 280° C and maintained at this temperature for two and a half hours. The autoclave is decompressed and allowed to cool while being maintained under an atmosphere of nitrogen. The polymer thus obtained has an intrinsic viscosity in formic acid of 1.42 (solution of 1 g of polymer in 100 cc of 75% formic acid was measured at 25°

C). It is impossible to extract the dyestuff from the polymer.

EXAMPLE 6

One operates as in Example 5, but 0.05 parts of acetic acid are added to the mixture. A spinnable polymer is obtained which has good properties. The threads obtained are red.

EXAMPLE 7

One operates as in Example 6, but the diamine of Example 1 is replaced by N,N'-bis(4-amino-bisphenyl)3,4-9,10-bis (dicarboximide)perylene. Brown filaments are obtained.

EXAMPLE 8

200 parts of water, 1.6 parts of sodium hydroxide, 0.5 parts of sodium laurylsulphate, 2.26 parts of hexamethylenediamine and 0.02 parts of N,N'-bis(4-amino-2-nitro-or 3-nitrophenyl)-1,8,4,5-bis(dicarboximide)naphthalene are introduced with vigorous stirring into an apparatus provided with a stirring device. Vigorous stirring is effected at the ambient temperature for 2 minutes, then a solution of 3.66 parts of adipoyl dichloride in 100 parts of tetrachloroethylene is introduced over a period of 15 seconds, and the mixture is maintained at the ambient temperature for two and a half minutes while stirring. The product is filtered off and washed to remove mineral products. A copolyamide is thus obtained from which it is impossible to separate the constituents and which gives yellow filaments.

EXAMPLE 9

One operates as in Example 8, but on the one hand, the hexamethylenediamine is replaced by 2.10 parts of paraphenylenediamine and, on the other hand, the adipoyl dichloride is replaced by 4.06 parts of terephthaloyl dichloride. A yellow copolyamide is obtained.

EXAMPLE 10

95 parts of ε-caprolactam, 4.8 parts of hexamethylene-ammonium adipate and 0.2 parts of the mixture consisting of the cis form of the dyestuff of formula:

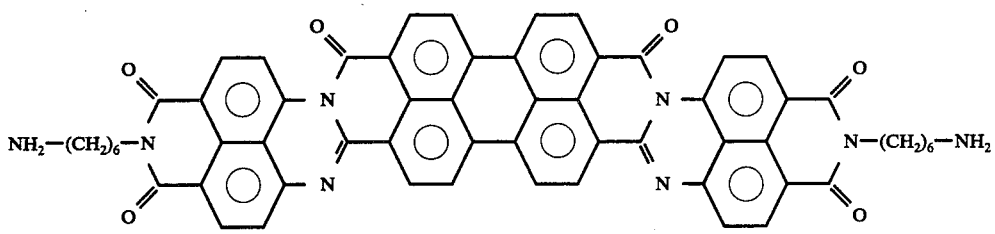

vacuum for about 30 minutes under 1 mm/Hg. The copolycondensate obtained gives blue filaments.

EXAMPLE 11

A mixture composed of 99.9 parts of 11-aminoundecanoic acid and 0.1 parts of the dyestuff of Example 10 (mixture of the cis and trans forms) is heated to 205° C. When water vapor is no longer evolved, the product is maintained for about 30 minutes under a vacuum of 1 mm/Hg. A blue copolycondensate is obtained.

EXAMPLE 12

One operates as in Example 5, but 49.95 parts of hexamethylene-ammonium sebacate and 0.05 parts of an equimolecular mixture of sebacic acid and of the dyestuff consisting of the mixture of the cis form of formula:

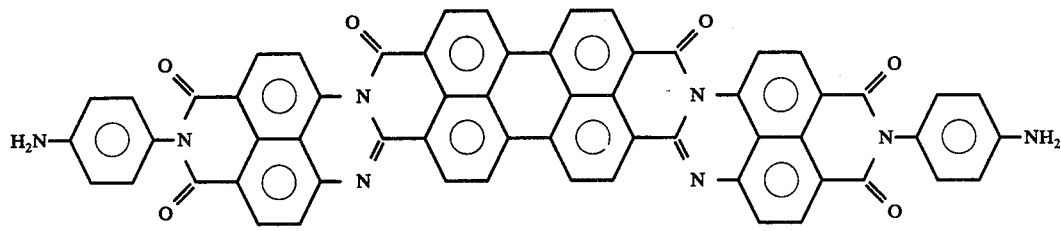

and the trans form of the same perinone are used.

A polymer is obtained which has an intrinsic viscosity in sulphuric acid of 0.90 (solution of 1 g of polymer in 100 cc of 96% $H_2SO_4$ - measured at 25° C).

EXAMPLE 13

One operates as in Example 8, but 220 parts of water, 0.82 parts of sodium hydroxide, 0.1 parts of sodium laurylsulphate, 1.16 parts of hexamethylenediamine, and 0.01 parts of N,N'-bis-aminoperylene-bis 3,4-9,10-dicarboximide) are used. The organic phase consists of 2.39 parts of sebacoyl dichloride in 150 parts of tetrachloroethylene.

A copolyamide of rose color is obtained.

What is claimed is:

1. Process for the coloration of a linear polyamide which comprises effecting polycondensation of at least one amide monomer and a pigment that is insoluble in organic solvents, said pigment being of the polycyclic polycarboximide series containing 2 primary amine or haloformyl functional groups, wherein the pigment has the formula:

and the trans form of the same perinone, are heated to 265° C in an inert atmosphere. This temperature is maintained for 6 to 8 hours and the mixture is kept under

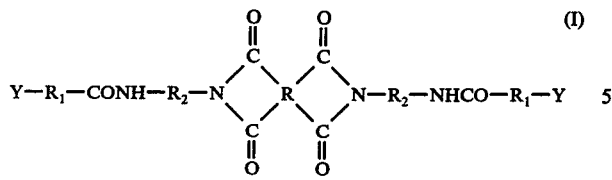
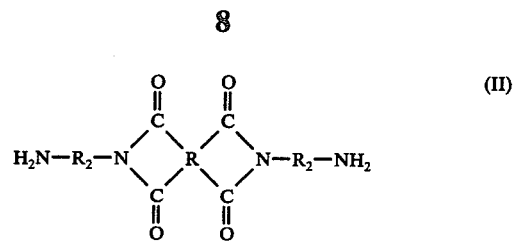

wherein R represents the tetravalent residue of a substituted mono- or poly-cyclic aromatic hydrocarbon or a substituted or unsubstituted perinone, $R_1$ represents a substituted or unsubstituted aliphatic, benzene, naphthalene or heterocyclic radical, $R_2$ represents a substituted or unsubstituted aliphatic, aromatic or heterocyclic radical and Y represents an amino or haloformyl group; said pigment being copolycondensed in the polymer chain of said polyamide; wherein the proportion of said pigment is from 1%. (1 to 1000) to 2% (2 per 100) by weight of the monomer or monomers; and said at least one monomer is selected from the group consisting of 11-amino-undecanoic acid; ε-caprolactam; p-phenylenediamine, decamethylenediamine or hexamethylenediamine together with terephthalic, isophthalic, adipic or sebacic acid.

2. Process for the coloration of a linear polyamide which comprises effecting polycondensation of the monomer or monomers and a pigment that is insoluble in organic solvents, said pigment being obtained by condensing a compound of the formula (I) given in claim 1 wherein Y is a haloformyl group with a diamine of the formula:

wherein R and $R_2$ have the meanings given in claim 1; said pigment being copolycondensed in the polymer chain of said polyamide.

3. Process according to claim 2 wherein the proportion of pigment is from 1% (1 to 1000) to 2% (2 per 100 ) by weight of the monomer or monomers.

4. A copolycondensate obtained according to the process claimed in claim 1.

5. A copolycondensate obtained according to the process claimed in claim 2.

6. A copolycondensate obtained according to the process for the coloration of a linear polyamide which comprises effecting the polycondensation of amide monomer or monomers and a pigment having the formula:

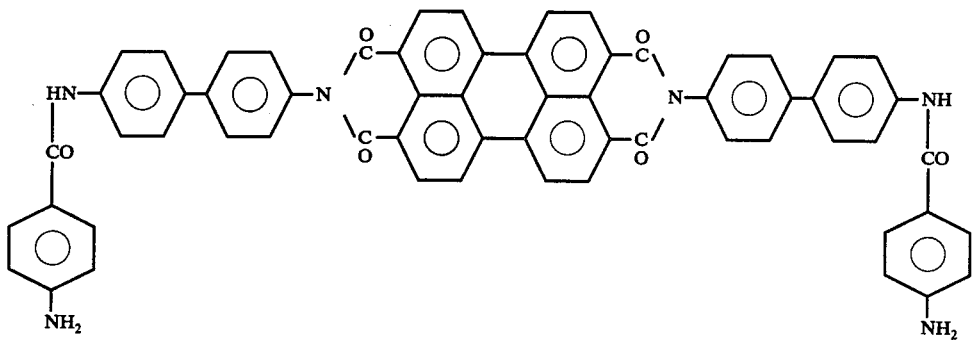

7. A copolycondensate obtained according to the process for the coloration of a linear polyamide which comprises effecting the polycondensation of amide monomer or monomers and a pigment having the formula:

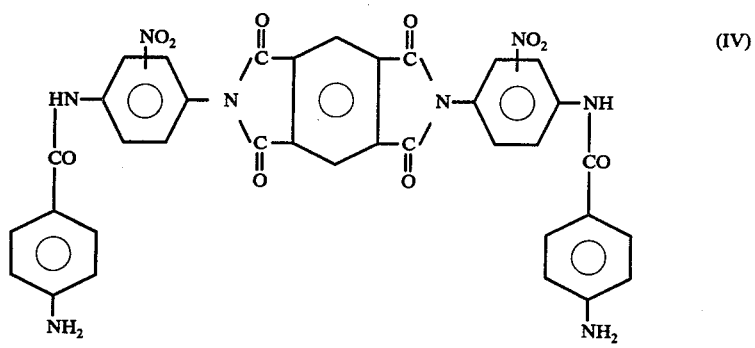

8. A copolycondensate obtained according to the process for the coloration of a linear polyamide which comprises effecting the polycondensation of amide monomer or monomers and a pigment having the formula:

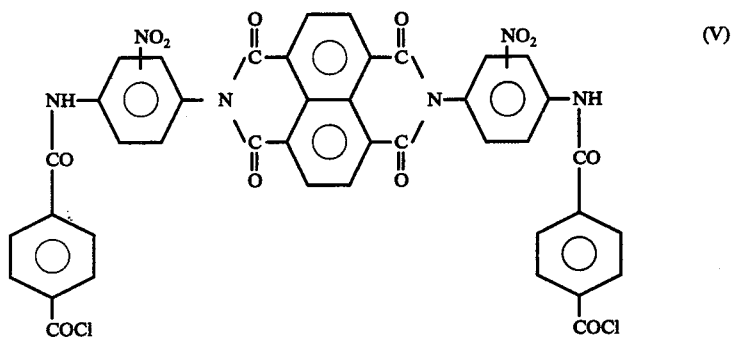

(V)

9. A copolycondensate obtained according to the process for the coloration of a linear polyamide which comprises effecting the polycondensation of amide monomer or monomers and a pigment consisting of a mixture of a cis form having the formula:

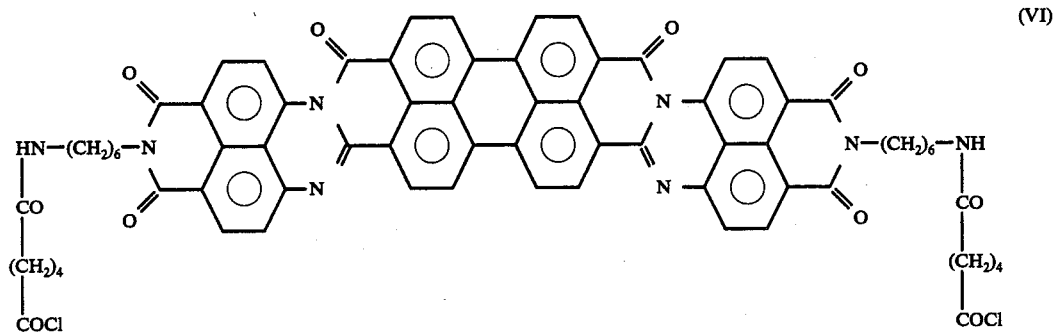

(VI)

and of the trans form thereof.

10. A copolycondensate obtained according to the process for the coloration of a linear polyamide which comprises effecting the polycondensation of amide monomer or monomers and a pigment which is a hexaimide resulting from the reaction of 1 mole of the dichloride of formula (V) in claim 11 with 2 moles of a diamine of the formula:

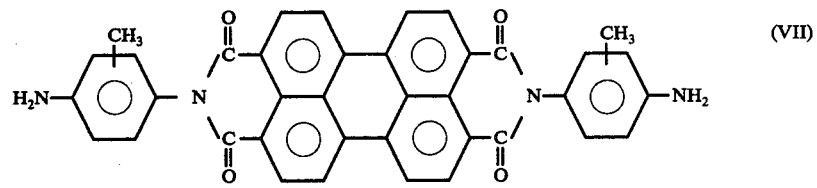

(VII)

* * * * *